United States Patent
Kim et al.

(10) Patent No.: US 9,514,513 B2
(45) Date of Patent: Dec. 6, 2016

(54) ESTABLISHING COMPATIBILITY BETWEEN TWO- AND THREE-DIMENSIONAL OPTICAL COHERENCE TOMOGRAPHY SCANS

(75) Inventors: Jong S. Kim, Pittsburgh, PA (US); Hiroshi Ishikawa, Pittsburgh, PA (US); Joel S. Schuman, Pittsburgh, PA (US); Gadi Wollstein, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 679 days.

(21) Appl. No.: 13/056,510

(22) PCT Filed: Aug. 6, 2009

(86) PCT No.: PCT/US2009/052951
§ 371 (c)(1),
(2), (4) Date: Apr. 7, 2011

(87) PCT Pub. No.: WO2010/017356
PCT Pub. Date: Feb. 11, 2010

(65) Prior Publication Data
US 2011/0176716 A1     Jul. 21, 2011

Related U.S. Application Data

(60) Provisional application No. 61/087,426, filed on Aug. 8, 2008.

(51) Int. Cl.
*A61B 3/10* (2006.01)
*G06T 3/00* (2006.01)

(52) U.S. Cl.
CPC ............. *G06T 3/0075* (2013.01); *A61B 3/102* (2013.01)

(58) Field of Classification Search
CPC ... A61B 3/102; A61B 5/0066; G01B 9/02091; G01B 9/02087; G06T 2207/10101; G06T 2207/30041; G06T 7/0012
(Continued)

(56) References Cited

U.S. PATENT DOCUMENTS 6,276,799 B1 * 8/2001 Van Saarloos et al. ...... 351/206
7,113,652 B2 * 9/2006 Reiners ......................... 382/291
(Continued)

OTHER PUBLICATIONS

Jiao et al., Simultaneous acquisition of sectional and fundus ophthalmic images with spectral-domain optical coherence tomography [on-line], Jan. 24, 2005 [retrieved Mar. 19, 2015], Optics Express vol. 13 Iss 2, pp. 444-452. Retrieved: http://www.opticsinfobase. org/oe/abstract.cfm?uri=OE-13-444.*
(Continued)

*Primary Examiner* — Matthew Bella
*Assistant Examiner* — Dennis Rosario
(74) *Attorney, Agent, or Firm* — Foley & Lardner LLP

(57) ABSTRACT

Advances in optical coherence tomography (OCT) have prompted a transition from time domain OCT, providing 2D OCT images, to spectral domain OCT, which has a 3D imaging capability. Yet conventional technology offers little toward the goal of inter-device compatibility between extant 2D OCT images and newer 3D OCT images for the same or comparable subjects, as in the context of ongoing monitoring the quantitative status of a patient's eyes. The inventive methodology is particularly useful to identify the scan location of tissue in a 2D OCT image within the 3D OCT volumetric data, thereby allowing clinicians to image a
(Continued)

patient via 3D OCT, based on available 2D OCT images, with minimal inter-device variation.

9 Claims, 21 Drawing Sheets

(58) Field of Classification Search
USPC .......................................... 382/131, 106, 128
See application file for complete search history.

(56) References Cited

U.S. PATENT DOCUMENTS

| | | | | |
|---|---|---|---|---|
| 7,301,644 | B2 * | 11/2007 | Knighton et al. | 356/479 |
| 7,365,856 | B2 * | 4/2008 | Everett et al. | 356/479 |
| 7,593,559 | B2 * | 9/2009 | Toth et al. | 382/128 |
| 7,747,062 | B2 * | 6/2010 | Chen et al. | 382/145 |
| 7,869,663 | B2 * | 1/2011 | Buckland et al. | 382/294 |
| 7,884,945 | B2 * | 2/2011 | Srinivasan et al. | 356/497 |
| 2006/0119858 | A1 | 6/2006 | Knighton et al. | |
| 2007/0025642 | A1 | 2/2007 | Buckland et al. | |
| 2007/0216909 | A1 | 9/2007 | Everett et al. | |

OTHER PUBLICATIONS

International Search Report PCT/US2009/052951 dated Mar. 12, 2010.

Wehbe et al., "Automatic retinal blood flow calculation using spectral domain optical coherence tomography," *Optics Express* 15(23), pp. 15193-15206 (2007).

Drexler et al., "Ultrahigh-resolution ophthalmic optical coherence tomography," *Nat. Med.*, 7(4), pp. 502-507 (2001).

Guedes et al., "Optical Coherence Tomography Measurement of Macular and Nerve Fiber Layer Thickness in Normal and Glaucomatous Human Eyes", *Ophthalmology*, vol. 110, Issue 1, pp. 177-189 (2003).

* cited by examiner

ESTABLISHING COMPATIBILITY BETWEEN TWO- AND THREE-DIMENSIONAL OPTICAL COHERENCE TOMOGRAPHY SCANS

CROSS-REFERENCE TO RELATED PATENT APPLICATIONS

This application claims priority from U.S. Provisional Application Ser. No. 61/087,426, filed Aug. 8, 2008, which is incorporated herein by reference in its entirety.

STATEMENT REGARDING FEDERALLY SPONSORED RESEARCH

This invention was made with United States government support under grant number RO1-EY013178-6, awarded by the National Institutes of Health. The United States government has certain rights in the invention.

BACKGROUND OF THE INVENTION

Optical coherence tomography (OCT) was developed in 1991 by D. Huang, J. Schuman and others at the Massachusetts Institute of Technology. OCT is a low-coherence, interferometer-based, noninvasive medical imaging modality that can provide non-contact, high-resolution, cross-sectional images of biological tissue.

The current global market for OCT systems is around $200 million and is growing at an annual rate of 34%. This expansion is expected to continue at pace for the next several years, with revenues topping $800 million by 2012. See Bio-Medicine.Org, 1-14-2008, at http://www.bio-medicine.org/medicine-news-1/Optical-Coherence-Tomography-Market-to-Top-24800-Million-by-2012-9502-1).

OCT can be divided into many different categories, such as time domain OCT (TD-OCT), time domain OCT with tracking (tracking OCT), polarization-sensitive OCT (PS-OCT), Doppler OCT, spectral domain OCT (SD-OCT), swept source OCT, and adaptive optics OCT. Recently, SD-OCT was commercialized with high resolution and faster acquisition time, compared to conventional TD-OCT such as 2D OCT. The multiple B-scans with SD-OCT provide volumetric data, which can be used to visualize comprehensive structural information, for example, of the retina and retinal pathologies with 3D rendering software in ophthalmology. The capabilities of OCT for quantitative analysis ability are important in this context, especially for glaucoma assessment. Retinal nerve fiber layer (RNFL) thickness measurements, performed via repeated OCT B-scans on the same subject, allow for tracking of developmental changes with glaucoma, which is globally the second leading cause of blindness. Follow-up scans are needed to detect RNFL thickness change, which may take months or years.

There has been no approach available to date that offered the prospect of compatibility between 2D OCT scan and 3D OCT volumetric data. Accordingly, a methodology is needed for establishing compatibility among different devices, by finding the same scan location of a 2D OCT cross-sectional image within follow-up, 3D OCT volumetric data. In particular, clinicians could use such a methodology to track, compare, and ultimately, without inter-device variation, detect any abnormal change that manifests over long periods of time.

SUMMARY OF THE INVENTION

It is an object of the present invention to provide a method to identify the scan location of tissue in a 2D OCT image within the 3D OCT volumetric data, thereby allowing clinicians to image a patient via 3D OCT, and compare them based on available 2D OCT images, with minimal inter-device variation.

One embodiment provides a method of establishing image registration between a two-dimensional optical coherence tomography image and a three-dimensional optical coherence tomography image, comprising the steps of: (A) obtaining the two-dimensional image via a pre-defined scanning protocol such that the two-dimensional image includes a portion of an eye; (B) obtaining the three-dimensional image such that the three-dimensional image includes said portion; then, (C) in the three-dimensional image, delineating a region of interest within said portion; then (D) re-sampling said region with said pre-defined scanning protocol to generate at least one two-dimensional re-sampled image; then, (E) in each of said two-dimensional image and said re-sampled image, detecting at least one feature of interest common to both images; then (F) correlating between said feature in said two-dimensional image and said re-sampled image, respectively, with respect to at least one similarity measure to identify a location on said feature in said two-dimensional image and said re-sampled image, respectively, wherein said location exhibits the highest value of said measure; and then (G) establishing image registration between said re-sampled image and said two-dimensional image, based on spatial information about said location.

DETAILED DESCRIPTION OF THE INVENTION

All the references cited herein in this Specification, including the descriptions of the figures, are incorporated by reference in their entirety.

Data Gathering

Figure 1:
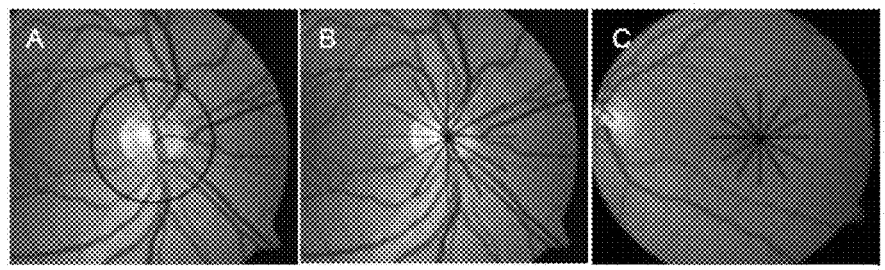
FIG. 1 shows visualization of Stratus OCT scanning protocols on fundus photo: A) circle scan; B) radial scan in on optic nerve heard; C) radial scan in on macular.

There are many different scanning protocols (or "patterns") with OCT imaging devices, as shown in FIG. 1, and OCT can be used to image different types of tissues or organs. For example, a scan pattern can be a circular scan or a radial scan. A circular scan is illustrated in FIG. 1A, whereas a radial scan is illustrated in FIGS. 1B and 1C. It is also generally known in the art that in OCT imaging an A-scan refers to an axial depth scan, a B-scan refers to a cross-sectional scan, and a C-scan refers to an enface imaging at an certain depth. As noted above, OCT can be used to scan a portion of an eye, such as the optic nerve head, or the blood vessels. In that context, clinical OCT systems in ophthalmology employ standardized OCT imaging protocols, whereby specific areas of the retina are scanned. Thus, glaucoma typically is assessed using an RNFL (circular) scan, which is useful for detecting RNFL thickness change over time (see FIG. 1A). In addition, an OCT optic nerve head (ONH) scan provides ONH surface topography in detail to detect glaucomatous development (see FIG. 1B). The ONH radial scan provides information similar to that obtained with a commercial scanning laser ophthalmoscope, such as the Heidelberg Retina Tomograph, product of Heidelberg Engineering (Heidelberg, Germany). A macular (radial) scan is also useful to obtain structural information in the macular region (see FIG. 1C). The macular scan is an important tool to visualize degeneration such as age-related macular degeneration (AMD), macular holes, or drusen.

Figure 2:
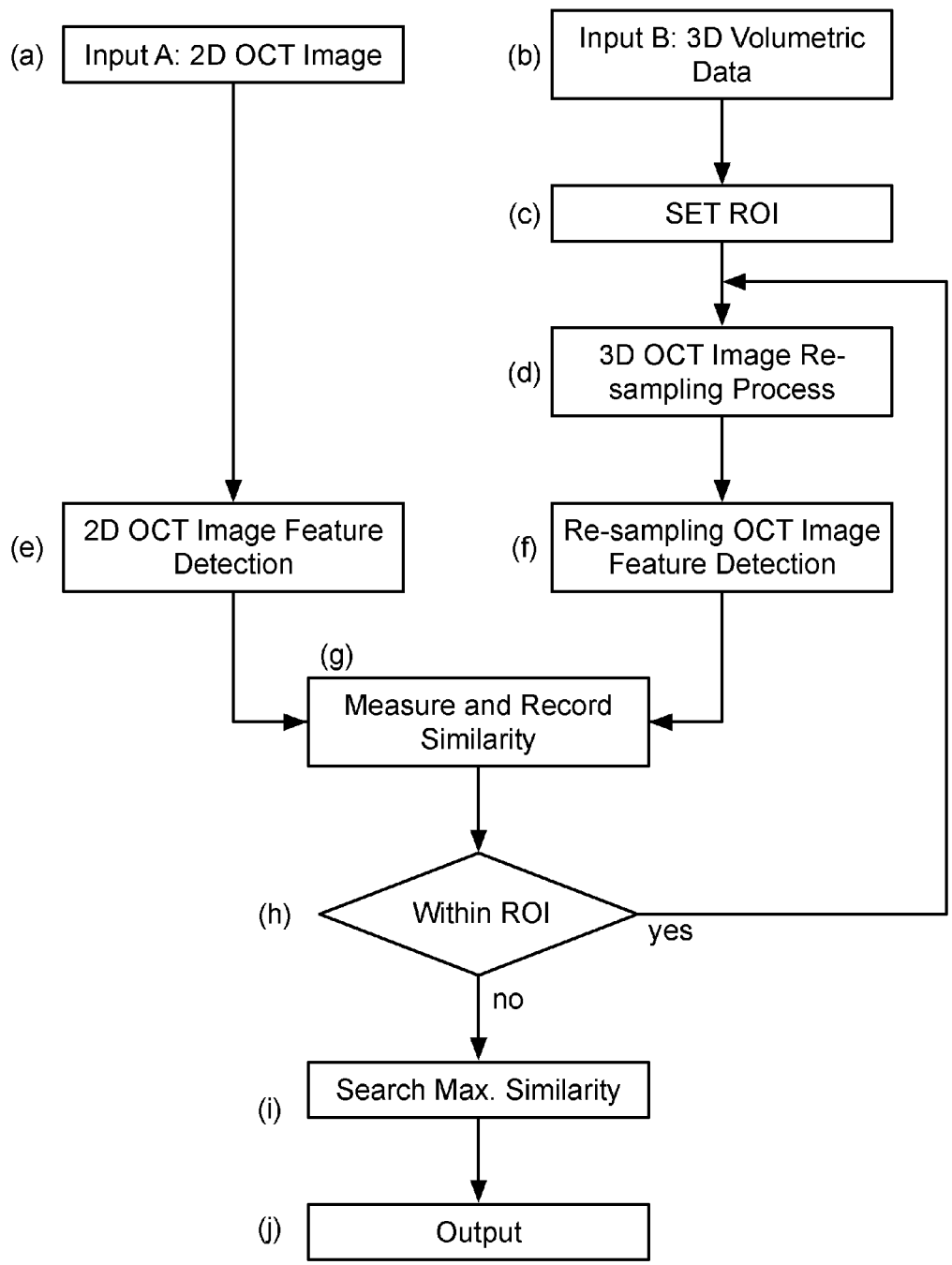
FIG. 2 shows visualization of data flow inside the system and sequence of operations.

A process for establishing registration between 2D and 3D OCT scans, according to the present invention, is illustrated in FIG. 2. First, a user defines scanning protocols (or "patterns") for obtaining both the input A (FIG. 2a) and the input B (FIG. 2b). The pre-defined patterns for the 2D and 3D scans, respectively, need not be the same. Subsequently, the user pre-defined scanning pattern of the input A will be used by a re-sampling process module (FIG. 2d) with 3D OCT volumetric data. The module mimics the pre-defined scanning protocol applied to 2D OCT imaging device. A pre-defined scanning pattern for 2D or 3D OCT scan contains full information of an OCT scan, including resolution of OCT image in pixels, radius of circular scan, each angle between scans from radial scan, region of scan (macular or optic nerve head), or combinations thereof.

Subsequently, a region of interest (RoI, FIG. 5) is defined by a user in the 3D OCT volumetric data. RoI delineates the boundary in an OCT image for similarity computation (FIG. 2g). Within the boundary, a user can then detect and define specific feature or features of interest for comparison of both the 2D OCT image and the re-sampled 2D OCT image generated by the re-sampling module (FIG. 2d).

Data Processing

1) Inputs: 2D OCT Image and 3D OCT Volumetric Data

In one embodiment of the invention, image inputs from at least two OCT devices are used for comparison with respect to at least one similarity measure between the images. Many different types of OCT devices are available commercially. Illustrative of a standard clinical ophthalmic OCT instrument is the Stratus OCT, a time domain OCT that is a product Carl Zeiss Meditec, Inc. (Dublin, Calif.). Since it has a scanning speed of 400 axial scans per second, the Stratus OCT can acquire a 512-axial scan (transverse pixel) OCT image in about 1.3 seconds. It has standardized OCT imaging protocols that scan cross-sections of specific areas of the retina in ophthalmology.

Figure 3:
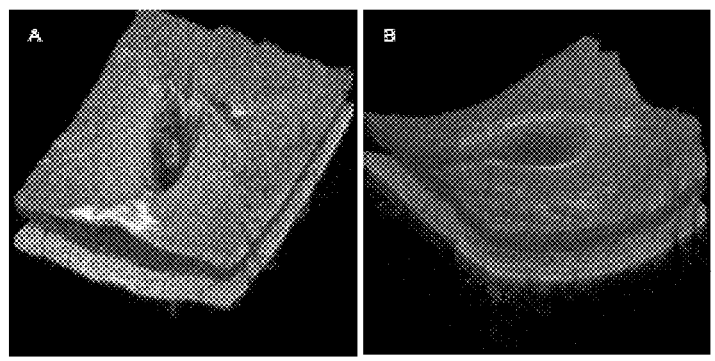
FIG. 3 illustrates 3D rendering of volumetric scans of A) optic nerve head and B) macular regions of normal subject.

The first input (FIG. 2a) can be a 2D OCT image in a single frame from a specific area of the retina. The second input (FIG. 2b) for the invention can be volumetric data (FIG. 3), acquired by a 3D OCT volumetric scan that contains the same region of the previous 2D OCT scan. There are various commercially available OCT devices that can provide such 3D volumetric scans, including time domain OCT with tracking, spectral domain OCT (SD-OCT), swept source OCT, or adaptive optics OCT.

2) 3D OCT Image Re-Sampling Process

The re-sampling module (FIG. 2d) can generate re-sampled 2D OCT image from 3D OCT volumetric data. The re-sampling of each axial scan (A-scan) line is determined by a pre-defined scanning pattern (i.e., by user input), which is the same scanning protocol used to obtain 2D OCT image as the first input (input A). Pursuant to the invention, this process can be performed once or iteratively within the user-defined RoI.

3) Feature Detection and Extraction

A feature can be any aspect of interest on the scanned subject in a given image, such as signal intensity distribution, shape, frequency spectrum, phase, or texture. In keeping with this invention, a feature detection method can comprise one technique or a combination of techniques, such as frequency domain image processing and spatial domain image processing. For instance, the method can comprise both of these or even additional techniques.

Frequency domain image processing is a method utilizing signal processing methods with Fourier transform, Cosine transform, or Hartley transform. Spatial domain image processing is a method utilizing image content directly such as thresholding, histogram analysis, color information, statistical operation, edge detection, shape matching, shape extraction, texture analysis, segmentation, classification method, or fuzzy processing. As it is illustrated in FIGS. 2e and 2f, the user-defined feature(s)s from two OCT images—2D OCT image (input A) and re-sampled 2D OCT image (input B)—are detected and extracted, respectively, by utilizing previously described image processing methods.

4) Measure and Record Similarity

Pursuant to the invention, features from two different OCT images, one from 2D OCT image (input A) and another from re-sampled image of 3D OCT volumetric data (input B), can be employed to obtain similarity measure(s) between two images. In general, a similarity measure can be, for example, the sum of absolute differences, cross-correlation, invariant moments, Euclidean distance, mutual information, or combinations thereof, of at least one parameter of two or more respective OCT images. Methods such as a segmentation algorithm can be useful to aide determination of similarity measures between the input A (FIG. 2a) and the re-sampled OCT image from the input B (FIG. 2b), in particular when the imaged subject comprises a retina. An illustrative segmentation method is described by Xu et al., *Automated Extraction of Optic Nerve Head Parameters from Spectral Domain Optical Coherence Tomography*, Poster No. 3659/D1049, presentation at ARVO 2008 Annual Meeting, Fort Lauderdale, Fla. (29 Apr. 2008), available at www.arvo.org. The similarity measure from the two images can be used to generate, for example, a correlation map.

A cross-correlation coefficient between A-scan lines, one from input A and another from the re-sampled image generated from the 3D OCT volumetric data, can be computed, summed, and recorded for the following module (FIG. 2g). The recorded cross-correlation coefficients can be used to generate a correlation map, which can be superimposed with the enface image for visualization purposes. Subsequently, similarity measures within any given RoI are recorded to find the most similar local region within 3D OCT volumetric data.

In theory, the magnitude of cross-correlation gets higher between very similar images as opposed to less similar images. There are outliers in reality, which reduces accuracy. Therefore, a probability function such as a 2D Gaussian probability density function can be multiplied with the cross-correlation map. The 2D Gaussian PDF function mimics the OCT operator's behavior. In the clinic, both 2D OCT and 3D OCT scans ideally should be centered at the RoI, such as the macula or optic nerve head (ONH). This is why the OCT operator tries to match both the scan location and RoI during scanning. This behavior can be expressed in a statistical term, called the probability density function (PDF). The PDF is a probability distribution of an event, which is scanning in this case. The probabilities of the event occurring within a given RoI is modeled by the PDF.

Additionally, a re-sampled OCT image from the sampling process may have artifacts in the image, resulting from relative eye motion during scanning along the A-scan line (axial depth) between input A and the re-sampled OCT image. This relative eye motion can be corrected, for example, by alignment through correlating each A-scan line of the re-sampled image to the 2D OCT image.

5) Search Maximum Similarity

FIG. 2i finds the most similar local region within the 3D OCT volumetric data to establish image registration by cross-correlation via comparing similarity measures, which were recorded throughout a given RoI. Pursuant to one embodiment of the invention, the cross-correlation map is multiplied with the 2D PDF to determine the highest similarity between the 2D OCT fundus and the 3D OCT fundus, thereby to find the maximum value from the 2D cross-correlation map. The highest similarity between the 2D OCT image as input A and the re-sampled OCT image as input B from 3D OCT volumetric data can be determined by, for example, finding the maximum value from correlation map. Spatial information (e.g., X-Y coordinates, angle, or scale) of the similar local regions is transmitted to the output module (FIG. 2j).

6) Output

Based on such spatial information, the output module (FIG. 2j) generates the final output in a pre-determined format, which is the same as the initial, user-defined scanning pattern, thereby establishing image registration. A pre-determined format can be a cross-sectional image along the re-sampling pattern and/or the center point (X-Y coordinates) of the re-sampling pattern. Thus, if the user wants to find the center point of a 3.4 mm-diameter re-sampling circle of 3D OCT volumetric data (input B), which shows the highest similarity with 2D OCT image (input A), then the corresponding point can be generated in X-Y coordinates.

NON-LIMITING WORKING EXAMPLES

Example 1

Using Enface Image Information

This illustrative method utilizes an OCT fundus (i.e., enface) image, which is one of the OCT image features, to obtain similarity measures between the input A and the re-sampled OCT image from the input B.

Figure 4:
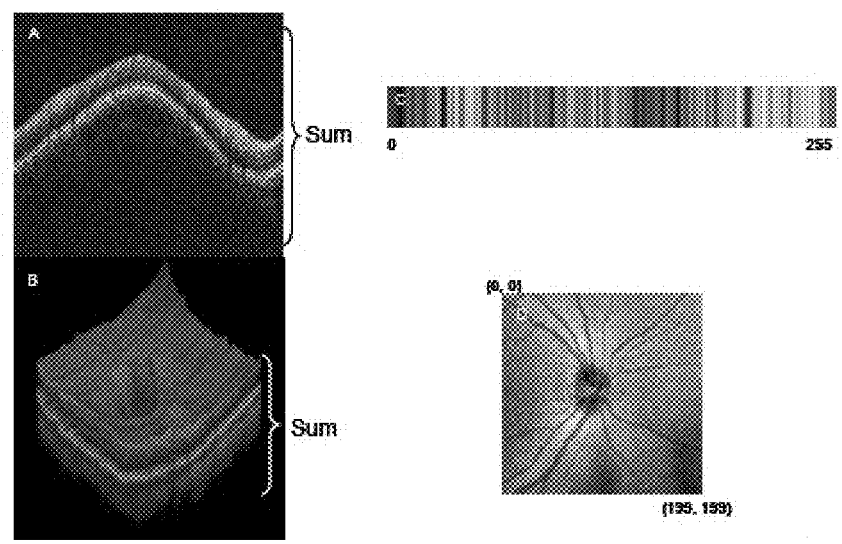
FIG. 4 illustrates visualization of enface image generation from both 2D OCT image and 3D OCT volumetric data: A) 2D OCT "Fast retinal nerve fiber layer (RNFL) Scan"protocol; B) 3D OCT volumetric data; C) single line enface image of A); D) enface image of B).

1. Pre-Processing and Input Images (FIGS. 2a and 2b)
2. OCT Fundus (Enface) Image Generation from Both Devices, 2D OCT and 3D OCT An OCT view of the fundus can be produced directly from 2D and 3D OCT data. The OCT fundus image is similar to that obtained by fundus photography or scanning laser ophthalmoscopy. The OCT fundus image is generated by summing each A-scan line (FIG. 4). The 3D OCT fundus image can be generated by summing the 3D OCT volumetric data along the axial direction at each transverse point on the retina (FIGS. 4B and 4D). A brightness value is generated for each axial scan, at each transverse position on the retina, which corresponds to the total backscattering or back-reflected light from all of the retinal layers at that position. For example, one of the Stratus OCT scanning protocols, "Fast RNFL scan," is a circular scan centered on the ONH with a 3.4 mm diameter and has 256(W)×1024(D) pixel in resolution. Cirrus HD-OCT (Carl Zeiss Meditec, Inc., Dublin, CA) has a raster scanning protocol for both macular and optic nerve head regions. This raster scanning protocol generates 200(W)×200(H)×1024(D) voxels. Therefore, single 256 pixels from Stratus OCT can be obtained. Cirrus HD-OCT will provide 200 tomograms, each containing 200 axial scans, with 1024 pixels in each a-scan. A single frame in the 3D OCT created by the Cirrus HD-OCT is one of these 200 tomograms; all 200 tomograms comprise the 3D OCT.

Figure 5:
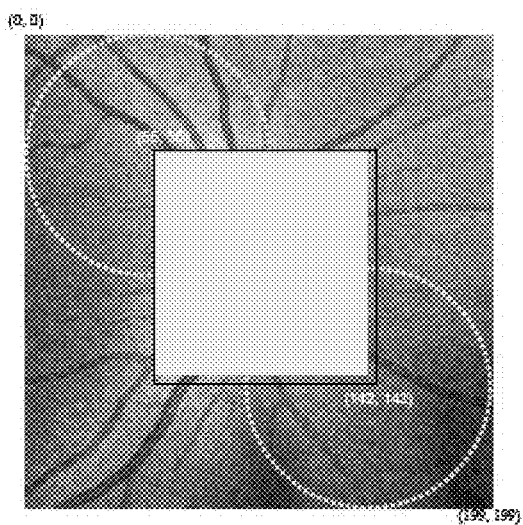
FIG. 5 illustrates search boundary of a given 3D OCT volumetric data.
Figure 6:
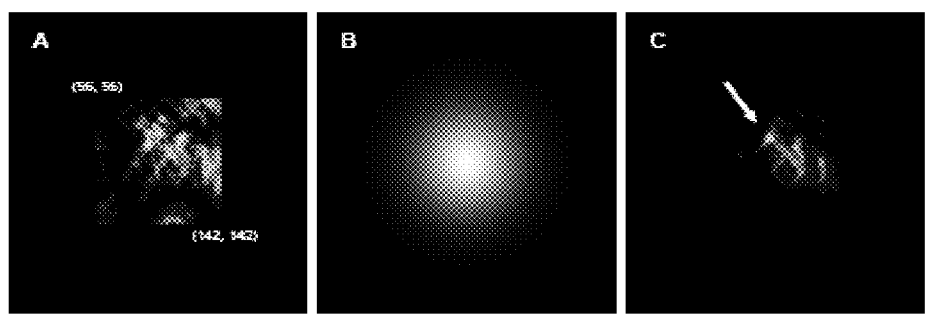
FIG. 6 shows correlation map multiplication with a Probability Density Function (PDF): A) correlation map after cross-correlation computation; B) 2D Gaussian PDF; C) point to point multiplication as performed with A) and B). White arrow indicates the maximum correlation value, which means that re-sampled cross-sectional image centered at the peak is the most similar to a given 2D OCT image.

3. Re-Sampling Process in 3D OCT Volumetric Data and Correlation (Similarity) Computation The same 2D OCT scanning protocol is mimicked within 3D OCT scan boundary (FIG. 5). The fundus image generated from Stratus OCT can be cross-correlated to the re-sampled 3D OCT fundus image. The 3.4 mm diameter is equivalent to about 114 pixels in the Cirrus HD-OCT fundus image. The cross-correlation value (R-square) at each center point of the 3.4 mm diameter circle is recorded and becomes a cross-correlation map at the end of process (FIG. 6). When the computation of cross-correlation at each center point on Cirrus HD-OCT fundus image is done, a peak location can be found on a cross-correlation map, which is related to maximum similarity between the 2D OCT fundus and re-sampled OCT fundus within 3D OCT fundus.

4. Correlation Mapping and 2D Probability Density Function as a Weighting Function A 2D Gaussian PDF (FIG. 6B) is multiplied with a cross-correlation map (FIG. 6A). The resultant, 2D Gaussian PDF function mimics the OCT operator's behavior. In a clinical context, as noted above, both 2D OCT and 3D OCT scans preferably are centered at the region of interest (RoI) such as the macula or optic nerve head (ONH).

5. Determination of Possible Scan Location of 2D OCT Image within 3D OCT Volumetric Data When the cross-correlation map is multiplied with the 2D Gaussian PDF, the highest similarity between the 2D OCT fundus and the 3D OCT fundus can be determined by finding the maximum value from the 2D cross-correlation map. Once the X-Y coordinate of the maximum cross-correlation point is determined, re-sampling along the 3.4 mm-diameter circle within 3D OCT volumetric data is performed to obtain a cross-sectional image (B-scan), which can be used to track, compare, and detect abnormal changes of the retina in clinic.

Example 2

Using A-Scan Line Information

This method utilizes each A-scan line information, which is one of the OCT image features, to obtain similarity measures between the input A and the re-sampled OCT image from the input B.

1. Pre-Processing and Input Images (FIGS. 2a and 2b).
2. Generating OCT Fundus Image for Visualization Purpose from 3D OCT Volumetric Data.

Figure 7:
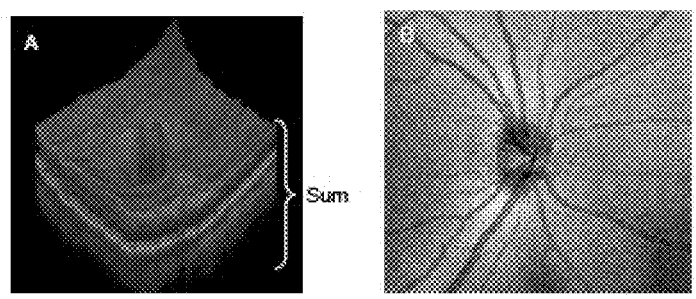
FIG. 7 shows visualization of enface image generation from 3D OCT volumetric data: A) 3D rendered OCT volumetric data; B) enface image generated by summing intensity values along each A-scan line.

OCT fundus image is generated by summing the 3D OCT volumetric data along the axial direction at each transverse point on the retina (FIG. 7). This generates a brightness value for each axial scan, at each transverse position on the retina, which corresponds to the total backscattering or back-reflected light from all of the retinal layers at that position. For example, Cirrus HD-OCT has a raster scanning protocol for both macular and optic nerve head regions. This raster scanning protocol generates 200(W)×200(H)×1024(D) voxels, which provides 200 tomograms, each containing 200 axial scans (A-scans), with 1024 pixels in each A-scan. A single frame in the 3D OCT created by the Cirrus HD-OCT is one of these 200 tomograms; all 200 tomograms comprise the 3D OCT.

3. Re-Sampling Process in 3D OCT Volumetric Data

Figure 8:
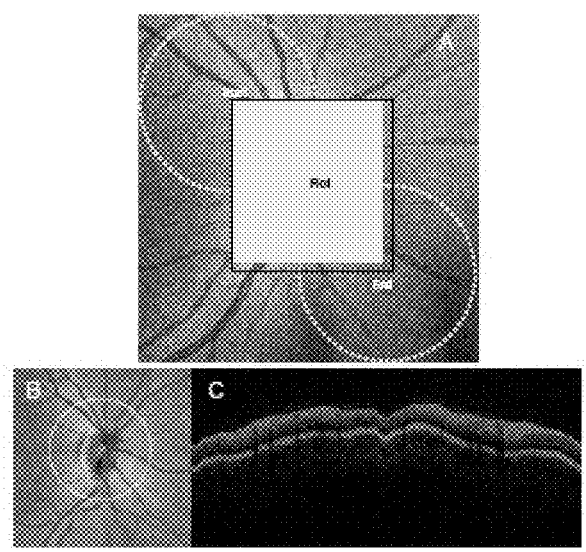
FIG. 8 shows A) search boundary or region of interest ("RoI") of a given 3D OCT volumetric data with 3.4 mm diameter circle scan; B) enface image generated from 3D OCT volumetric scan; C) re-sampled OCT image along the virtual circle (white circle) on enface image. Re-sampled OCT image is wavy due to eye motion during OCT scan.

The same 2D OCT image scanning protocol is mimicked within the 3D OCT scan boundary (FIG. 8). This module can generate a re-sampled OCT image from 3D OCT volumetric data by using the input A (FIG. 2a) scanning protocol. For example, a 3.4 mm diameter circle scan can be mimicked by drawing virtual 3.4 mm diameter circle on 3D OCT volumetric data (FIG. 8A) and by copying each A-scan line profile along a virtual circle with the same resolution (sampling density) as the 2D OCT image as the input A (FIG. 2a).

4. Relative Eye Motion Correction

Figure 9:
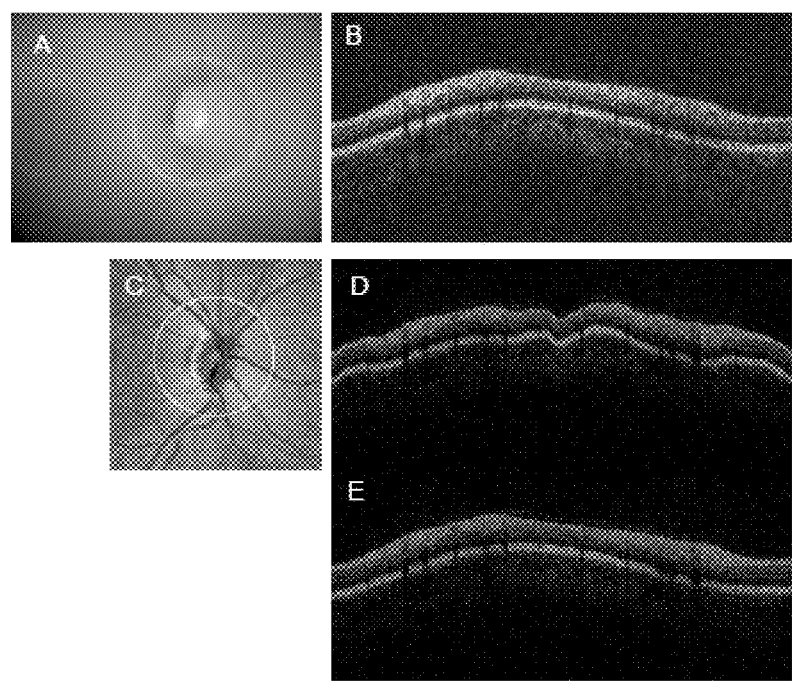
FIG. 9 provides a demonstration of correcting for relative eye motion: A) Stratus OCT fundus photo shows the location of actual scan; B) cross-sectional image along the circle (gray) on Stratus OCT fundus photo; C) enface image generated from 3D OCT volumetric scan; D) cross-sectional image along the circle (white) on enface image; E) cross-sectional image after relative eye motion correction.

Re-sampled OCT image from sampling process may have artifacts in the image resulting from relative eye motion during scanning along A-scan line (depth) between the input A (FIG. 9B) and re-sampled OCT image (FIG. 9D). This relative eye motion can be corrected by correlating each A-scan line of re-sampled image to the 2D OCT image (FIG. 9E).

5. Cross-Correlation Computation and Recording

Figure 10:
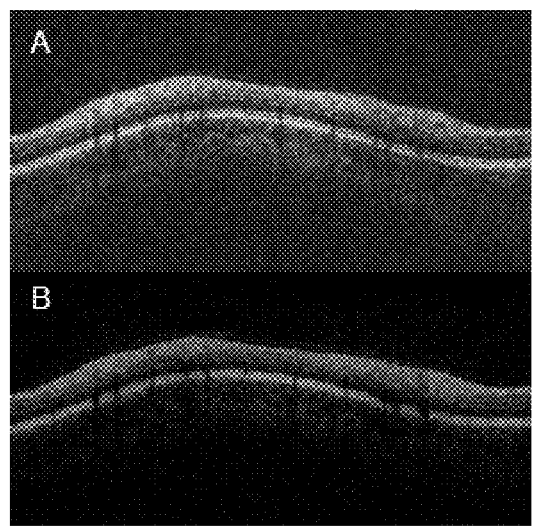
FIG. 10 provides cross-sectional images from A) Stratus OCT as an input and B) after a relative eye motion correction process: cross-correlation coefficient between A-scan lines, one from Stratus OCT image and another from re-sampled image from 3D OCT volumetric data, is computed, summed, and recorded.

Cross-correlation coefficient between A-scan lines, one from the input A (FIG. 10A) and another from re-sampled image (FIG. 10B) of 3D OCT volumetric data, can be computed, summed, and recorded for the following module (FIG. 2g). The recorded cross-correlation coefficients can be used to generate a correlation map (FIG. 11C), which can be superimposed over the enface image for visualization purposes.

6. Determining Possible Scan Location of 2D OCT Image within 3D OCT Scan

Figure 11:
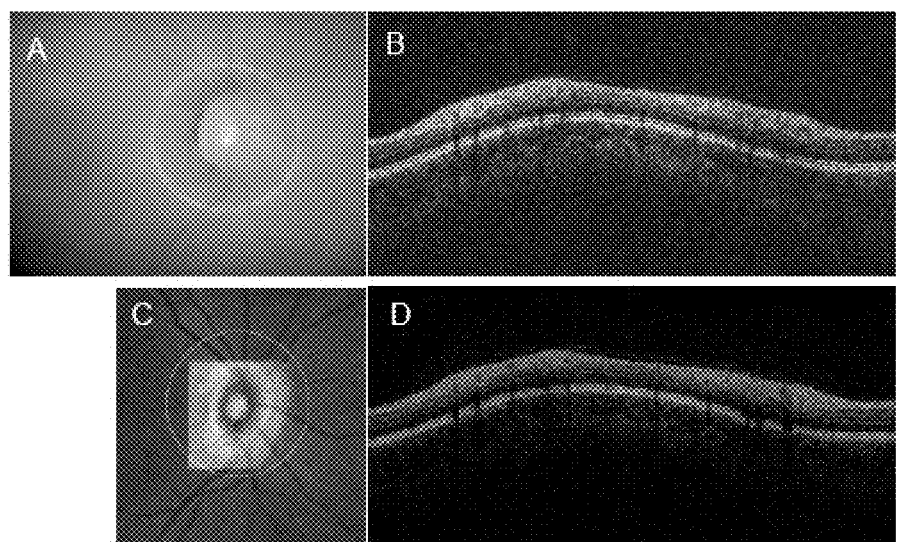
FIG. 11 shows estimated 2D OCT scan location in enface images: A) Stratus OCT fundus photo shows the location of actual scan; B) cross-sectional image along the circle (gray) on Stratus OCT fundus photo; C) enface image generated from 3D OCT volumetric scan and superimposed with correlation map; D) cross-sectional image along the circle (gray) centered at the peak (white) of correlation map in enface image.

The highest similarity between the 2D OCT image as the input A and the re-sampled OCT image as the input B from 3D OCT volumetric data can be determined by finding the maximum value from correlation map (FIG. 11C). Once the X and Y coordinates of maximum correlation are determined, re-sampling along the 3.4 mm diameter circle within 3D OCT volumetric data is performed to obtain a cross-sectional image (B-scan), which can be used to track, compare, and finally detect abnormal change of the retina in clinic.

Example 3

Other Features of Interest

The following methods illustrate other features from OCT images that can be used to obtain similarity measures. These methods may also be possible ways to realize this invention in clinic.

1. Retinal Tissue Segmentation

Figure 12:
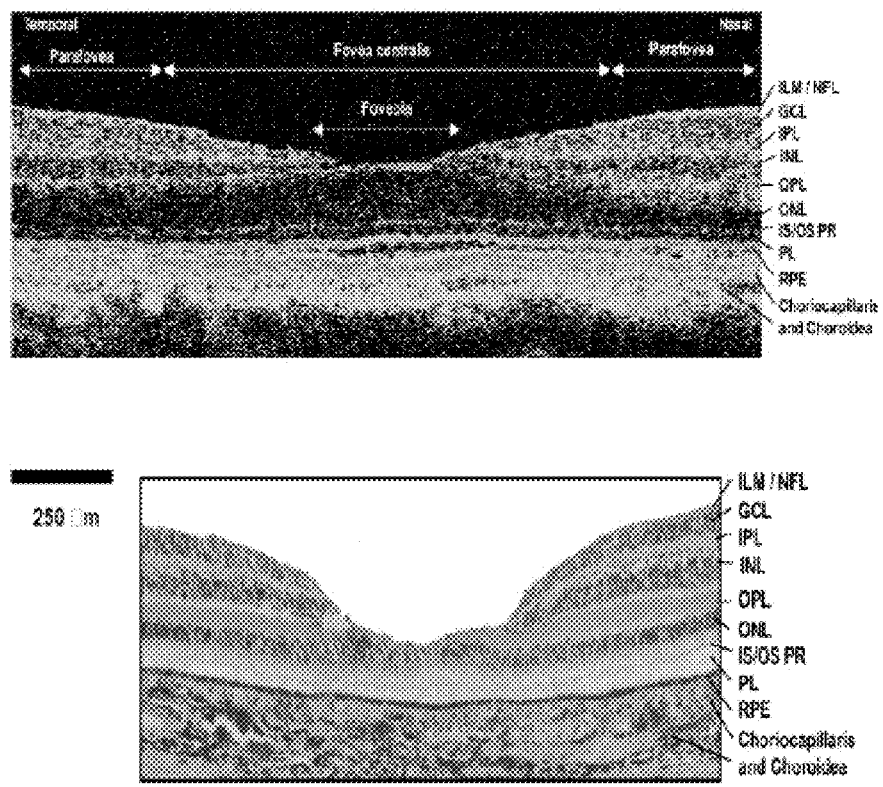
FIG. 12 shows histological cross-section of the retina (fovea) and OCT image (image taken from Drexler et al., *Nat Med* 2001: 7(4): 502-7).
Figure 13:
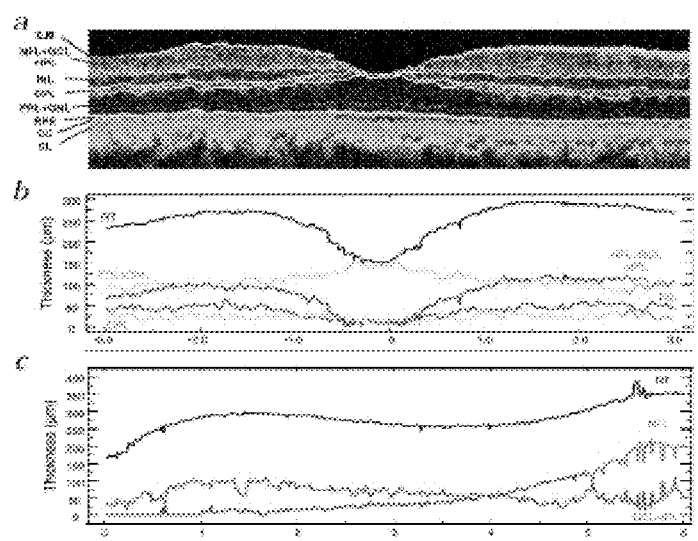
FIG. 13 shows quantification of intraretinal structures using a segmentation algorithm. (Image taken from Drexler et al., *Nat Med* 2001: 7(4): 502-7).
Figure 14:
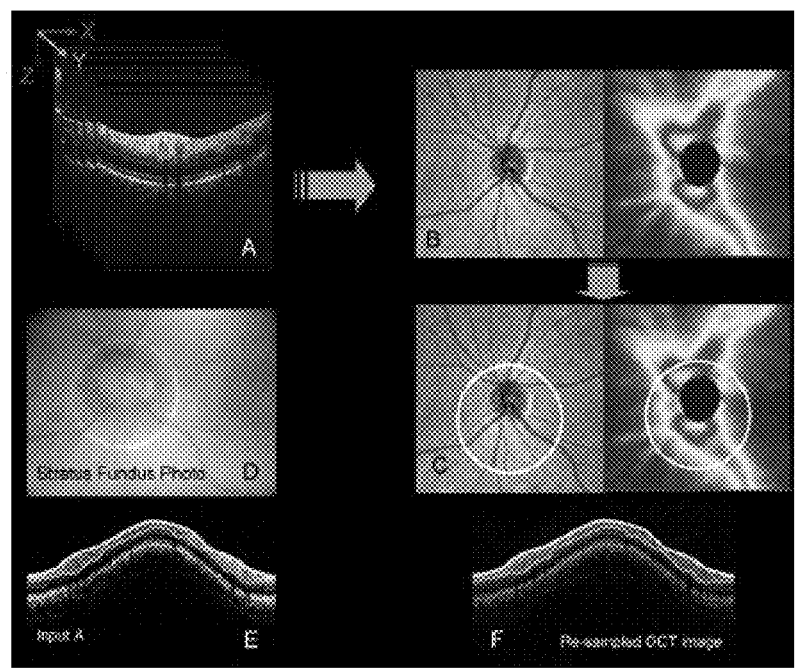
FIG. 14 provides illustration of a segmentation algorithm based comparison between the thickness of retinal nerve fiber layer (RNFL) obtained by Stratus OCT (E) and that obtained by 3D OCT re-sampled image (F): A) 3D OCT volumetric scan with segmented RNFL; B) RNFL thickness map (pseudo color); C) matched scan location (white circle) based on RNFL thickness comparison; D) Stratus OCT.

This method utilizes a segmentation algorithm to obtain similarity measures between the input A (FIG. 2a) and the re-sampled OCT image from the input B (FIG. 2b). As noted, such a segmentation method is described by Xu et al. (2008), supra. FIG. 13 shows how a cross-sectional OCT image of the retina (FIG. 12) can be segmented and quantized in clinic. The similar measurements of the retina layers (e.g., ILM, RNFL, RPE) can be expected when both the input A and re-sampled OCT images from the input B are very similar to each other. FIG. 14 illustrates how this method can be implemented in practice.

2. Vessel Matching Based on Vessel Detection Algorithm

Figure 15:
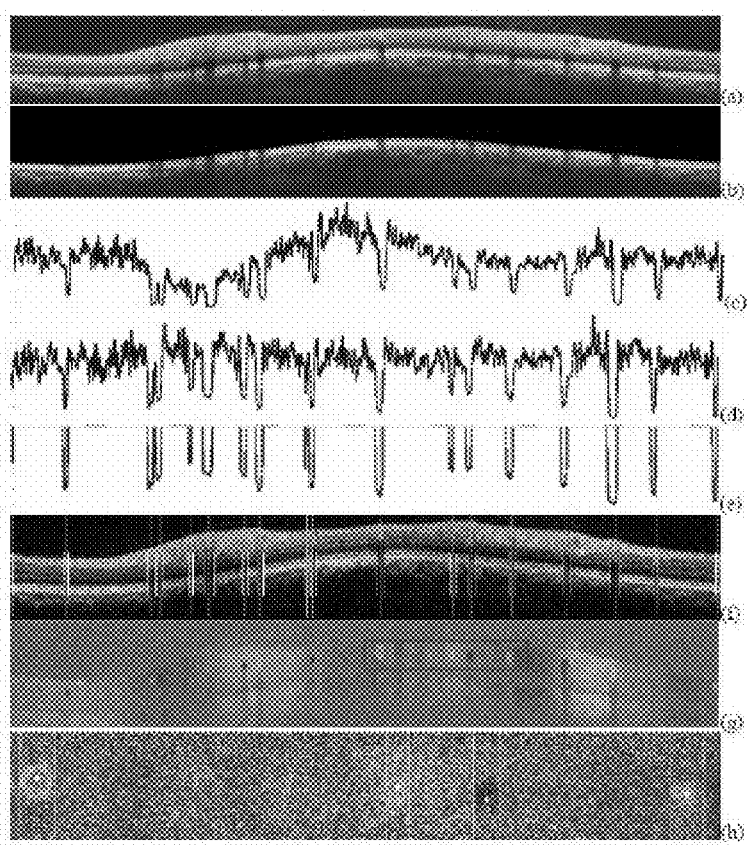
FIG. 15 provides images of retinal blood flow using spectral domain OCT; (A) high density circular scan (8192 A-lines) around the optic nerve head; (B) the OCT image after removal of the surface layers; (C) the original shadowgraph; (D) the shadowgraph after background correction and normalization; (E) the shadowgraph after thresholding; (F) recognized blood vessel centers and boundaries are marked on the OCT image; (G) the ODT image for the same OCT scan; (H) magnified view of the region marked in (G) where the calculated blood vessel centers are marked. (Images are taken from Wehbe et al., *Optics Express* 15 (23), 15193-15206).
Figure 16:
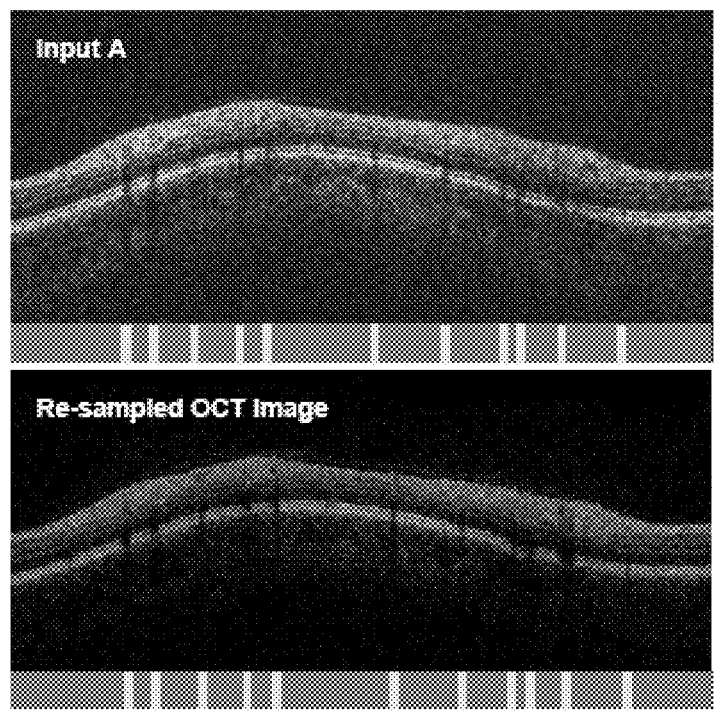
FIG. 16 shows vessel locations on both TD-OCT image as the input A and the re-sampled OCT image as the input B: bars with similar intervals under each image can be observed. Slight variation exists due to eye motion.

This method utilizes vessel information to obtain similarity measures between the input A (FIG. 2a) and the re-sampled OCT image from the input B (FIG. 2b). Vessel related information can be, for example, location of vessel and velocity of blood flow contained on OCT cross-sectional image. Optical Doppler tomography (ODT) is one of many optical coherence tomography technologies, which can measure the velocity of blood flow by measuring the Doppler shift (FIG. 15). In addition, the results of ODT can be used to locate vessels as locations of flow. FIG. 16 shows vessel locations on both images. They are very similar when two cross-sectional images are coming from the same location. Slight variations between the two images exist because scan quality can be different or eye motion can introduce distortion of the 3D OCT scan due to a long scanning time, about 1.48 seconds per scan with the Cirrus HD-OCT (Carl Zeiss Meditec, Inc., Dublin, Calif.) compared to eye motion occurring in fractions of seconds. Furthermore, a vessel detection algorithm can be used directly to detect and record this feature.

3. Stratus OCT Fundus Photo Based Matching

Figure 17:
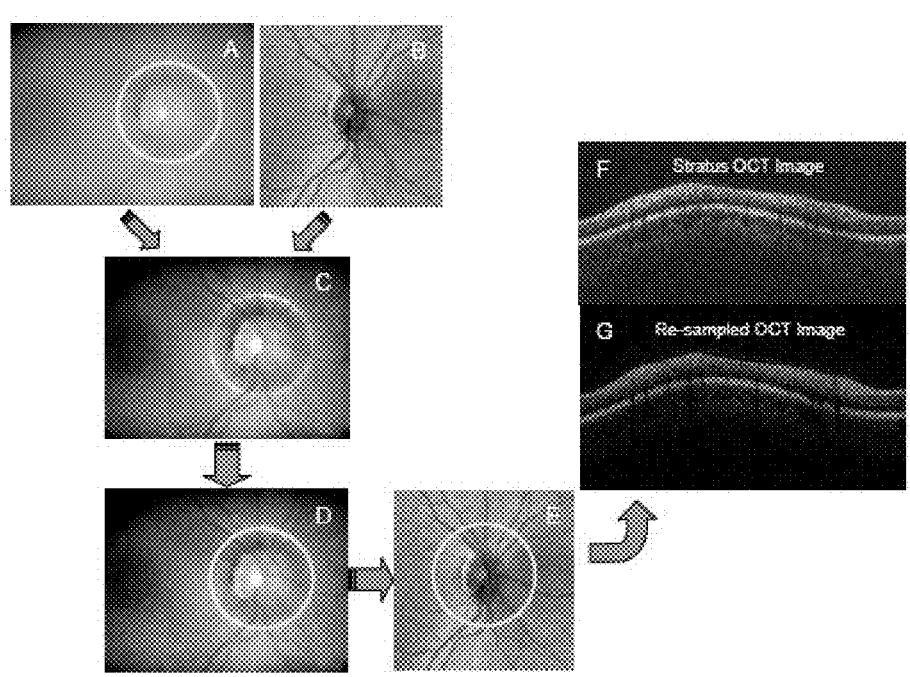
FIG. 17 provides illustration of Stratus OCT fundus photo based matching: A) Stratus OCT fundus photo with circular scan, which centered at an optic nerve head (ring); B) enface image from 3D OCT cube data; C) registration of both A) and B) with scaling, rotation, and X-Y translation; D) and E) exported scan location (ring) to enface image; F) and G) Stratus OCT image and re-sampled OCT image, respectively, from the same location.

A fundus photo generated by an infrared (IR) camera of Stratus OCT can be used to estimate possible scan location because the IR image is taken just after OCT scanning and contains the scan location and scanning pattern in general. First, the fundus image of 2D OCT and OCT fundus (enface) image from 3D OCT volumetric scan can be registered together. Scan location (FIG. 17A, yellow ring) on fundus photo of 2D OCT can be exported to OCT enface image (FIG. 17E, ring). Finally, re-sampled OCT image (FIG. 17G) can be obtained from the same location within the 3D OCT volumetric scan (FIG. 17E).

Results

Figure 18:
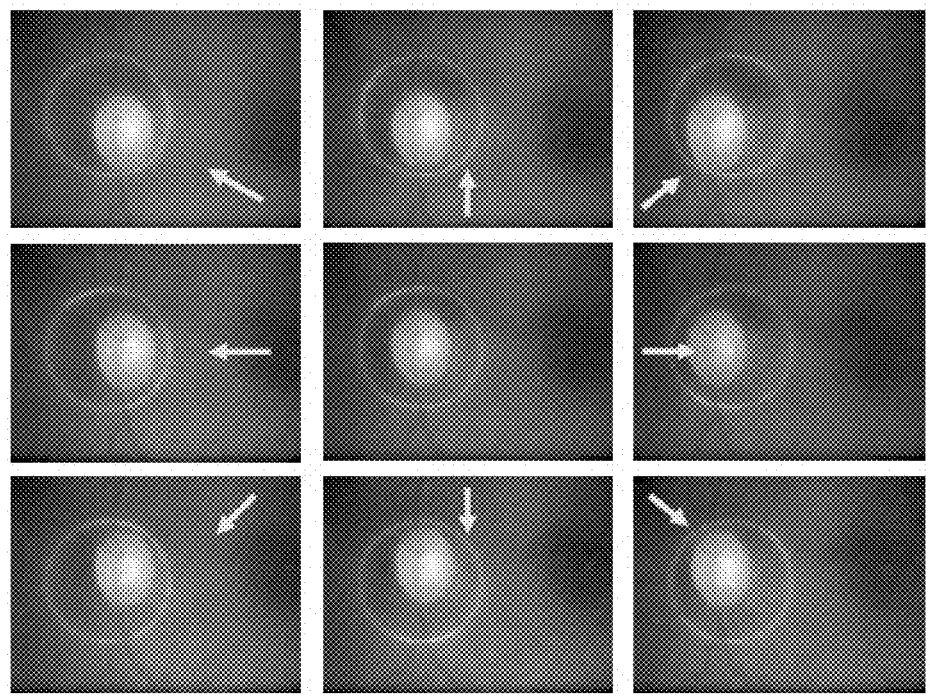
FIG. 18 shows illustration of nine different scan locations for one eye.
Figure 19:
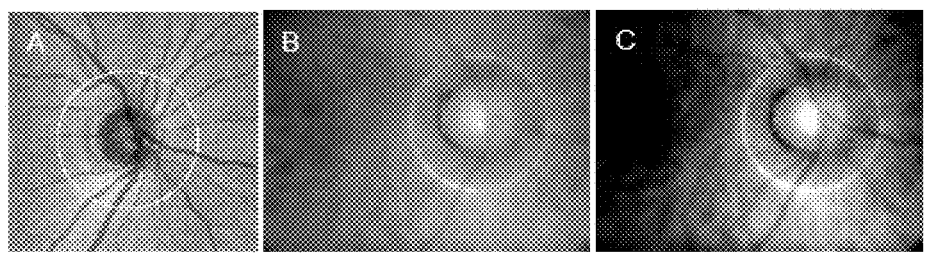
FIG. 19 shows a 3D OCT enface image (A) and Stratus OCT fundus photo (B) registered in (C). Yellow background in (C) is the matched region of 3D OCT enface image.
Figure 20:
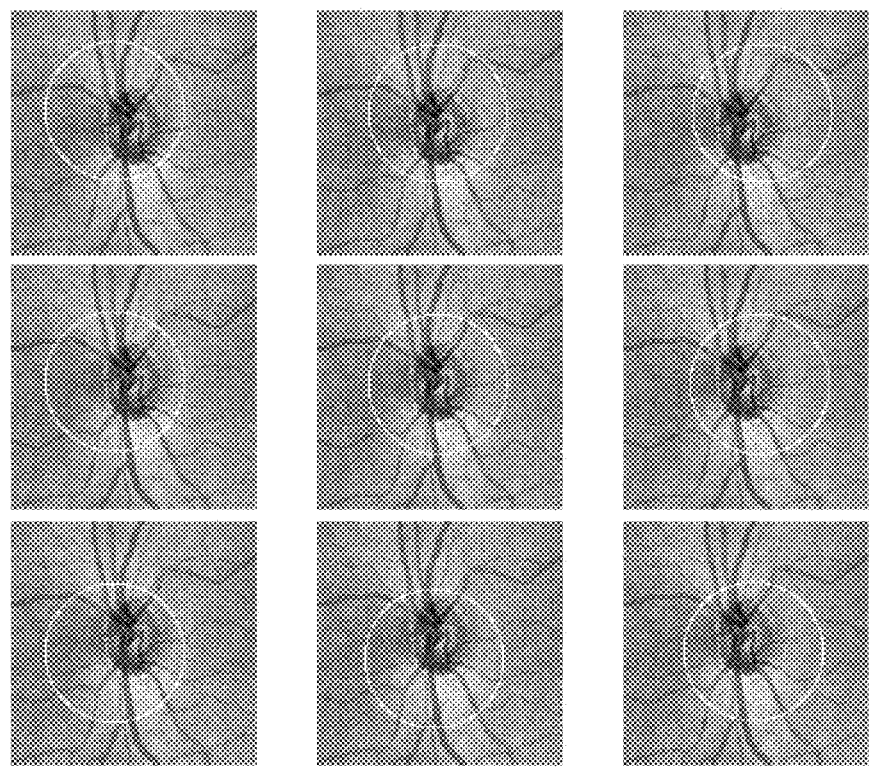
FIG. 20 shows matched results on 3D OCT enface images using FIG. 18 data as the inputs.

Nine scans with various scan locations from 11 eyes of 11 subjects were collected (see FIG. 18). Stratus OCT fundus images from nine different locations were manually registered, adjusting for translation and rotation (FIG. 19) with Cirrus HD-OCT enface images (FIG. 20) with computed scan location within 3D OCT volumetric scan by matching major vessels. Secondly, the distance between the center points of the two different circles was measured. Finally, overall mean and standard deviation (SD) of the distances, which is a measurement error of this invention, were computed.

The overall mean and SD of the distances between fundus circles and located circles on the 3D OCT dataset were 2.56±1.55 pixels in Cirrus HD-OCT enface image (200(W)×200(H)), which is substantially equivalent to 76.8±46.5 μm in the retina. This error is relatively small compared to the OCT enface image size.

Figure 21:
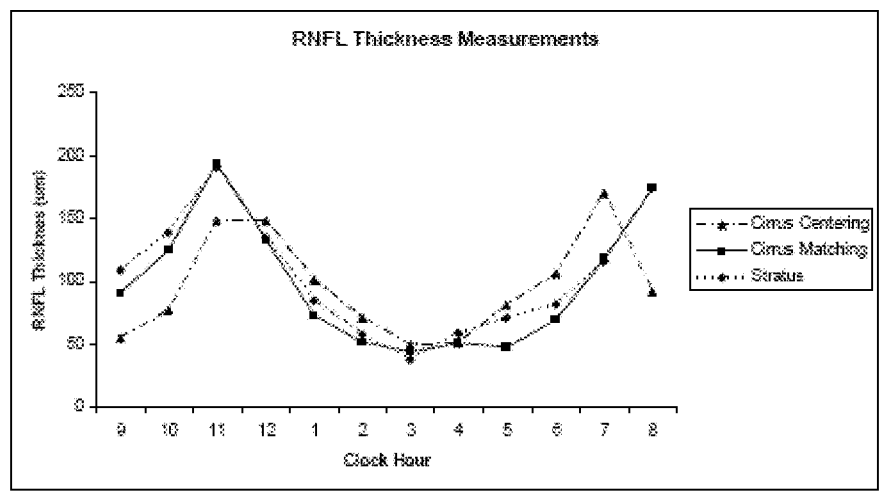
FIG. 21 shows RNFL thickness measurements (upper) from three different methods: Stratus OCT scan, Cirrus optic disc centered re-sampling (Cirrus Centering), and Stratus scan matched Cirrus re-sampling (Example 1 in Detailed Description). The bottom graph shows difference between Cirrus centering and Cirrus matching (Example 1). Cirrus matching method shows lower RNFL thickness measurement variation compared to Cirrus centering method.
Figure 21:
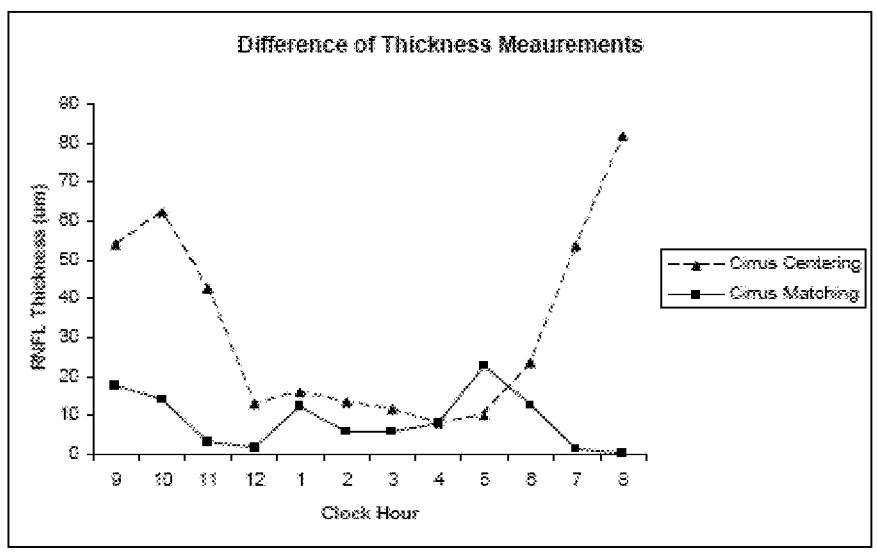

In addition, three different RNFL thickness measurements from three different methods, using Stratus OCT circle scan or Cirrus HD-OCT optic disc centered re-sampling (commercial software version 3.0), were compared and images were matched, using the approach as described in Example 1. First, six scans with various scan locations from both eyes and the same subject were collected. FIG. 21 shows RNFL thickness measurements obtained from the different methods. The bottom graph shows a difference between Cirrus optic disc centering (automatic disc centering using commercial software) and Cirrus matching, as shown in Example 1. The invention achieved lower RNFL thickness measurement variation, compared with the Cirrus optic disc centering method.

What is claimed is:

1. A method of establishing image registration between a two-dimensional optical coherence tomography (OCT) image and a three-dimensional optical coherence tomography image, comprising the steps of:
   (A) obtaining, with a first type of OCT device, the two-dimensional image using a pre-defined scanning protocol such that the two-dimensional image includes a portion of an eye;
   (B) obtaining, with a second type of OCT device different than the first type of OCT device, the three-dimensional image such that the three-dimensional image includes said portion; then,
   (C) in the three-dimensional image, delineating a region of interest within said portion; then
   (D) re-sampling said region of interest using said pre-defined scanning protocol to generate at least one two-dimensional re-sampled image; then,
   (E) in each of said two-dimensional image and said re-sampled image, detecting at least one feature of interest common to both images; then
   (F) correlating between said feature in said two-dimensional image and said re-sampled image, respectively, with respect to at least one similarity measure to identify a location on said feature in said two-dimensional image and said re-sampled image, respectively, wherein said location exhibits the highest value of said measure; and then
   (G) establishing image registration between said re-sampled image and said two-dimensional image, based on spatial information about said location.

2. The method of claim 1, wherein step (E) further comprises frequency domain image processing or spatial domain image processing, or a combination thereof.

3. The method of claim 1, wherein step (F) further comprises multiplying a two-dimensional Gaussian probability density function with a cross-correlation map.

4. The method of claim 1, wherein the step (F) further comprises correcting artifacts in said re-sampled image resulting from eye motion during step (B).

5. The method of claim 1, wherein said similarity measure is a sum of absolute differences, cross-correlation, invariant moments, Euclidean distance, mutual information, or combinations thereof.

6. The method of claim 1, wherein said spatial information is selected from the group consisting of X-Y coordinates, angle, scale, and combinations thereof.

7. The method of claim 1, wherein the pre-defined scanning protocol involves scanning the portion in a circular pattern.

8. The method of claim 1, wherein the second type of OCT device obtains the three-dimensional image using a second scanning protocol.

9. The method of claim 1, wherein the second scanning protocol is different than the pre-defined scanning protocol.

* * * * *

UNITED STATES PATENT AND TRADEMARK OFFICE
CERTIFICATE OF CORRECTION

PATENT NO.       : 9,514,513 B2
APPLICATION NO.  : 13/056510
DATED            : December 6, 2016
INVENTOR(S)      : Jong S. Kim et al.

Page 1 of 1

It is certified that error appears in the above-identified patent and that said Letters Patent is hereby corrected as shown below:

In the Specification

In Column 1, Lines 15-18, replace:
"This invention was made with United States government support under grant number RO1-EY013178-6, awarded by the National Institutes of Health. The United States government has certain rights in the invention."

With the following:
--This invention was made with United States government support under grant numbers EY013178 and EY008098 awarded by the National Institutes of Health. The United States government has certain rights in the invention.--

Signed and Sealed this
Twenty-fifth Day of December, 2018

Andrei Iancu
*Director of the United States Patent and Trademark Office*